United States Patent [19]
Brokish

[11] Patent Number: 5,929,312
[45] Date of Patent: Jul. 27, 1999

[54] DENT CORN HYBRID 5953

[75] Inventor: Harold A. Brokish, Champaign, Ill.

[73] Assignee: Kleinwanzlebener Saatzucht AG, Germany

[21] Appl. No.: 08/909,787

[22] Filed: Aug. 12, 1997

[51] Int. Cl.$^6$ .............................. A01H 5/100; A01H 1/00; A01H 4/00; C12N 5/04

[52] U.S. Cl. ...................... 800/320.1; 800/298; 800/275; 435/410; 435/411

[58] Field of Search ..................................... 800/200, 250, 800/DIG. 56; 435/410, 411

[56] References Cited

U.S. PATENT DOCUMENTS 5,491,295  2/1996  Niebur et al. ............................... 47/58

OTHER PUBLICATIONS

"UI team targets old corn disease," *Business & Agriculture*, pp. C1–C2 (Jul. 27, 1997).
Promotional Information from Pioneer: "Pioneer Brand Products for 1994–95".
Promotional Information from Pioneer: "Crop Notes 1995–96".
Promotional Information from Pioneer: "Hybrids that bring it home".
Promotional Information from Great Lakes Hybrids: "5962".

*Primary Examiner*—Gary Benzion
*Assistant Examiner*—Ousama Zaghmout
*Attorney, Agent, or Firm*—Townsend and Townsend and Crew, LLP

[57] ABSTRACT

This invention is in the field of corn breeding, specifically relating to a single cross dent corn hybrid designated as 5953. Hybrid 5953 is a variety especially bred for the north central United States having superior resistance to grey leaf blight.

7 Claims, No Drawings

DENT CORN HYBRID 5953

FIELD OF THE INVENTION

This invention is in the field of corn breeding, specifically relating to a single cross dent corn hybrid designated as 5953. Hybrid 5953 is a variety especially bred for the north central United States and has superior resistance to grey leaf blight.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, stalk strength, root strength, ear retention, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desire phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations, the heterozygous condition gives way to homogeneous lines as a result of self-pollination and selection. Typically in the pedigree method of breeding, five or more generations of selfing and selection is practiced: F1; F2; F3; F4; F5, etc. These selfing generations are sometimes designated as S0, S1, S2, etc with S0 being an equivalent to F1 while S2 is an equivalent to F3, etc.

Backcrossing can be used to improve an inbred line. Backcrossing transfers a specific desirable trait from one inbred or source to an inbred that lacks that trait. This can be accomplished, for example, by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the nonrecurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred parent lines, each of which has a genotype which complements the genotype of the other. The hybrid progeny of the first generation is designated F1. In the development of hybrids, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny (F1). During the inbreeding process in corn, the vigor of the lines decreases. Vigor is restored when two unrelated inbred lines are crossed to produce the hybrid progeny (F1). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). Much of the hybrid vigor exhibited by F1 hybrids is lost in the next generation (F2). Consequently, seed from hybrid varieties is not used for planting stock.

Corn is an important and valuable field crop. Thus, a continuing goal of plant breeders is to develop consistent performing, high-yielding corn hybrids that are agronomically sound based on stable inbred lines. The reasons for this goal are obvious: to maximize the amount of grain produced with the inputs used and minimize susceptibility of the crop to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few, if any, individuals having the desired genotype may be found in a large F2 or S1 population. Typically, however, the genotype of neither the parents nor the desired genotype is known in any detail. An agronomically acceptable F1 hybrid will come from a cross between two superior inbred parental lines. There is no assurance that either of these parental lines will produce a superior hybrid when crossed with a different inbred parent line. Thus, the selection or combination of the two parental inbreds provides a unique hybrid that demonstrates characteristics and performance levels that differ from that obtained when either of the parents is crossed with a different inbred parent line.

Once the superior combination of two parental lines is determined by the testing and selection of the F1 hybrid, that F1 hybrid and the performance traits and characteristics of the hybrid can be indefinitely reproduced so long as the parental inbreds are maintained in their homozygosity and the quality and production procedures are accomplished to the purity standards determined by the seed industry regulation.

At Great Lakes Hybrids, Inc., there are approximately 100,000 pollinations made in each breeding nursery for each generation. Winter research stations are utilized in Puerto Rico and Chile to increase the developmental progress that can be accomplished in a given year. At various generations in the development of the inbred lines, they are crossed to an appropriate tester to made experimental hybrids. These experimental hybrids are tested in the appropriate areas of adaptation in the United States. The testing is conducted through the use of replicated test plots at several locations. Strip test plots are utilized as the hybrids approach commercial utilization.

SUMMARY OF THE INVENTION

This invention provides for hybrid corn seed designated as 5953 and having ATCC Accession No. 203075. The invention also includes the corn plants produced by the seed of hybrid 5953. In addition, this invention provides for a corn plant having the physiological and morphological characteristics of the plant of hybrid 5953.

This invention also provides for tissue cultures of regenerable cells of a plant derived directly or indirectly from hybrid 5953 especially where the tissue regenerates into plants having all or essentially all of the important morphological and physiological characteristics of hybrid 5953. The plants regenerated from the tissue culture cells derived from hybrid 5953 are also a part of this invention.

Finally, hybrid seed produced utilizing the genetic contributions of a plant or plants derived from hybrid 5953 and having fifty percent or more of the genotype hybrid 5953 are expressly included in this invention.

DETAILED DESCRIPTION

According to the invention, there is provided a novel single cross dent corn hybrid, designated 5953. Hybrid 5953 has been especially bred for the north central United States. In addition to matching or exceeding the phenotypes of other commercially available varieties with regard to characteristics of yield and vigor, hybrid 5953 has particularly good resistance against grey leaf blight.

Grey leaf blight has become an increasing concern in the north central United States because of the recent increase in the practice of minimal tilling. The practice of minimal tilling has become increasingly common in order to minimize soil loss due to erosion. However this practice tends to increase last year's leaf debris on the surface of the soil. This debris serves as a source of carryover inoculum for grey leaf blight. In the past, conventional cultivation practices would have buried last year's plants and the current year's corn exposure to leaf blight spores would be minimized.

Hybrid 5953 is the F1 resulting from crossing the parental inbred lines, KW4632 and KW7616. This invention thus relates to the seeds of the single cross corn hybrid 5953, to the plants of the single cross corn hybrid 5953, and to the production of a resultant seed or corn plant by crossing the inbred line KW4632 with inbred line KW7616.

Great Lakes Hybrids, Inc. has developed in its research program a unique variety in the hybrid 5953. In the presentation of data and information, the uniqueness of 5953 is demonstrated by comparing it to the next closest prior art varieties. The next closest prior art varieties would be the related hybrids that are composed of at least 50% of the parent material utilized in the formation of hybrid 5953. In addition, we compared hybrid 5953 against commercially available varieties which were optimally selected for sale in the north central United States. Two varieties that are representative of the quality of the varieties currently available for the north central market are Pioneer's 3394 and Great Lake Hybrids' 5962.

The following data compares the performance of 5953 to hybrids that are most closely related. Table 1 compares 5953 to the related hybrids that have the same female parent as 5953, but with different male parents. Table 2 compares 5953 to the related hybrids that have the same male parent as 5953, but with different female parents. This is used to demonstrate that the most favorable combination of parental lines or components is the combination that forms the hybrid designated as Great Lakes 5953.

DEFINITIONS RELATING TO TABLE 1, TABLE 2 AND TABLE 6

HYBRID. The single cross F1 combination produced by crossing two homozygous parent lines.

PEDIGREE. The names or designations for the homozygous parent lines used to form the Hybrid. The first parent line listed is the female parent followed by the male or pollinator parent.

LOC. The number of locations or test environments that were used in the collection of the data that is listed.

No. 2 YIELD. The shelled grain yield reported in bushels per acre based calculated at 15.5% moisture.

MOISTURE. The moisture is the actual percentage moisture of the grain at harvest.

POPUL. The population or plants per acre equivalent that are calculated from the physical count of the plants occupying the plot area.

% RL. The root lodging is the percentage of plants that root lodge; i.e., those that lean from vertical at an approximate angle of 30 degrees or more.

% SL. This is the percentage of plants that demonstrate lodging from natural forces. Lodging in this data is referred to as the breaking over of the plant below the upper ear node of attachment.

TW. Test Weight is the density weight of a standard bushel of shelled grain. This measurement is taken at the time of harvest.

DATA COMPARING 5953 TO RELATED
HYBRIDS

TABLE 1

| HYBRID | PEDIGREE | LOC | No. 2 YIELD | MOIS | POPUL | % RL | % SL | TW |
|---|---|---|---|---|---|---|---|---|
| 5953 | KW4632xKW7616 | 42 | 166.4 | 21.61 | 25,498 | 3.6 | 2.2 | 54.5 |
| 5962 | KW4632xKW7691 | 42 | 159.7 | 22.05 | 25,428 | 3.7 | 3.4 | 54.6 |
| 5953 | KW4632xKW7616 | 46 | 166.7 | 21.77 | 25,651 | 3.4 | 2.1 | 54.5 |
| 96446 | KW4632xKW7615 | 46 | 154.5 | 23.22 | 25,766 | 1.3 | 2.7 | 54.8 |
| 5953 | KW4632xKW7616 | 40 | 166.5 | 21.84 | 25,709 | 3.6 | 2.1 | 54.4 |
| 95407 | KW4632xKW7617 | 40 | 162.8 | 22.79 | 25,557 | 6.2 | 8.2 | 54.3 |

TABLE 2

| HYBRID | PEDIGREE | LOC | No. 2 YIELD | MOIS | POPUL | % RL | % SL | TW |
|---|---|---|---|---|---|---|---|---|
| 5953 | KW4632xKW7616 | 9 | 172.7 | 24.41 | 26,550 | 0.6 | 1.5 | 56.6 |
| 96488 | KW4646xKW7616 | 9 | 164.1 | 27.31 | 26,680 | 1.4 | 1.7 | 54.4 |
| 5953 | KW4632xKW7616 | 8 | 184.8 | 23.89 | 26,980 | 0.0 | 0.4 | 55.9 |
| 65106 | KW4608xKW7616 | 8 | 176.7 | 23.59 | 26,770 | 0.0 | 0.8 | 54.8 |
| 5953 | KW4632xKW7616 | 8 | 184.8 | 23.89 | 26,980 | 0.0 | 0.4 | 55.9 |
| 65105 | KW4713xKW7616 | 8 | 178.5 | 23.84 | 26,730 | 0.3 | 0.4 | 54.0 |

The results in Table 1 demonstrate that 5953 has higher yield than the related hybrids while showing a lower harvest moisture which is considered favorable. The percent of root lodging was improved with 5953 in some comparisons, but was not as favorable in other comparisons. The percent stalk lodging showed an improvement for 5953 over the related hybrids. Test weight was very similar in the comparisons.

The results of Table 2 demonstrate that 5953 has higher yield than the related hybrids while showing an equal or lower harvest moisture. The percent of root lodging was equal or improved in these comparisons. In no comparison was 5953 inferior for root lodging. The percent stalk lodging exhibited equal or slight improvement in the Table 2 comparisons. Test weight was higher in all comparison for this table. A higher test weight is considered more desirable.

The results in Table 1 and Table 2 reflect very positively on the merits of 5953. There may not be a statistical significance in the data for a particular trait, but the combination of improvements demonstrated by several of the traits provides a cumulative enhancement of the hybrids performance. This improved performance is desirable and makes 5953 superior to the next closest hybrids.

ELECTROPHORESIS COMPARISONS

Isoenzymatic studies were conducted by Biogenetic Services, Inc located at 2308 6th Street; Brookings, S. Dak. Isozyme data were generated for Hybrid 5953 according to the procedures described in Stuber, C. W., Wendle, J. F., Goodman, M. M., and Smith, J. S. C., "Techniques and Scoring Procedures for Starch Gel Electrophoresis of Enzymes from Maize (Zea mays L.)," Technical Bulletin No. 286, North Carolina Agricultural Research Service, North Carolina State University, Raleigh, N.C. (1988).

In summary, the enzymatic components of partially purified cell homogenates are separated using conventional electrophoretic techniques (starch gels). The banded enzymes are then stained using substrate specific labelling techniques. The various enzymes are identified in Table 3. By convention, the dual numerical data reflects the diploid nature of the plants with each allelic form being randomly designated a number. Accordingly ADH1 is designated 11 or 12 with 11 representing a homozygous plant having identical isozyme forms (actually appearing as a single band) and 12 representing a heterozygous individual having two forms of ADH1. By comparison with the prospective parent lines, this analysis permits one to confirm the parentage of the tested individuals.

TABLE 3

| GENOTYPE ANALYSIS | | | | | | | | | | | | |
|---|---|---|---|---|---|---|---|---|---|---|---|---|
| HYBRID | AD1 | AC1 | AC4 | MD1 | MD2 | ID2 | PG1 | PG2 | GL1 | PM2 | PH1 | CA3 |
| 5953 | 22 | 11 | 25 | 22 | 22 | 11 | 12 | 11 | 11 | 23 | 12 | 22 |
| 5962 | 22 | 13 | 25 | 22 | 12 | 11 | 12 | 11 | 15 | 22 | 12 | 22 |
| 96488 | 22 | 13 | 25 | 22 | 12 | 12 | 12 | 11 | 15 | 23 | 22 | 22 |
| HYBRID | EN1 | ES1 | ES4 | GO1 | GO2 | HX2 | ID1 | MD3 | MD4 | MD5 | Mmm | PR1 |
| 5953 | 33 | 13 | 23 | 22 | 11 | 22 | 22 | 11 | 11 | 11 | 11 | 22 |

TABLE 3-continued

GENOTYPE ANALYSIS

| | | | | | | | | | | | | |
|---|---|---|---|---|---|---|---|---|---|---|---|---|
| 5962 | 33 | 22 | 23 | 22 | 11 | 23 | 22 | 11 | 11 | 11 | 11 | 22 |
| 96488 | 33 | 13 | 13 | 22 | 11 | 22 | 22 | 11 | 11 | 11 | 11 | 12 |

KEY:

| | | | |
|---|---|---|---|
| AD1 = ADH1 | AC1 = ACP1 | AC4 = ACP4 | MD1 = MDH1 |
| MD2 = MDH2 | ID2 = IDH2 | PG1 = PGD1 | PG2 = PGD2 |
| GL1 = GLU1 | PM2 = PGM2 | PH1 = PHI1 | CA3 = CAT3 |
| EN1 = ENP1 | ES1 = EST1 | ES4 = EST4 | GO1 = GOT1 |
| GO2 = GOT2 | HX2 = HEX2 | ID1 = IDH1 | MD3 = MDH3 |
| MD4 = MDH4 | MD5 = MDH5 | Mmm = Mmm | PR1 = PRX1 |

Table 3 lists the electrophoresis identification for hybrid 5953. This table also reflects the close relationship of two related hybrids used in the presentation of the data in Table 1 and Table 2. The genotype analysis provided in Table 3 demonstrates that although 5953 has many similarities with the related hybrids, it clearly lists unique in its genetic composition.

MORPHOLOGICAL TRAITS

Table 4 lists the morphological traits for hybrid 5953 along with the traits of two of the hybrids that are close relatives to 5953. The two related hybrids were used in the data comparisons in Table 1 and Table 2 listed above. Table 4 indicates that there are differences that can be positively identified indicating that 5953 has some unique morphological traits when compared to the next closest genotypes. Table 4 also provides a morphological identification of several trait for hybrid 5953.

TABLE 4

| TRAIT | 5953 | 5962 | 95407 |
|---|---|---|---|
| Emergence Vigor | 3 | 3 | 3 |
| GDU 50% Pollen | 1326 | 1294 | 1350 |
| GDU 50% Silk | 1326 | 1268 | 1350 |
| Plant Color | MD | M | MD |
| Anther Color | YELLOW | L. PUR | YELLOW |
| Silk Color | REDDISH | SALMON | PALE GR |
| Leaf Orientation | 60 | 65 | 60 |
| Leaf Width | 10.0 | 9.5 | 10.0 |
| Number of Leaves | 6 | 5 | 6 |
| Tassel Type | 1 | 1 | 1 |
| Tassel Size | 5 | 5 | 9 |
| Tassel Length | 42.0 | 53.0 | 52.0 |
| Tassel Branch Number | 5 | 6 | 5 |
| Plant Height | 280 | 250 | 260 |
| Ear Height | 120 | 115 | 85 |
| Stalk Diameter | 25.0 | 25.2 | 21.3 |
| Shank Length | 6.2 | 9.0 | 9.1 |
| Husk Leaves | 0.0 | 0.0 | 0.0 |
| Ear Attitude | 1 | 1 | 1 |
| Glume Color | 1 | 1 | 1 |
| Glume Band Color | 1 | 4 | 1 |
| Anthocyanin TC | NO | NO | NO |
| Anthocyanin Base | NO | NO | NO |
| Anthocyanin in Nodes | YES | NO | YES |
| Intactness Rating | 4 | 6 | 5 |
| Ear Type | CYLINDRIC | CYLINDRIC | CYLINDRIC |
| Kernel Rows | 16 | 16 | 16 |
| Kernel Width | 7.5 | 7.7 | 8.0 |
| Kernel Length | 12.5 | 12.2 | 12.2 |
| Kernel Thickness | 4.0 | 4.0 | 4.0 |
| Cob Diameter | 27.5 | 26.5 | 27.5 |
| Cob Color | RED | RED | DK RED |
| Weight of 100 Kernels | 40.0 | 41.8 | 43.3 |
| Grain Texture | MED HRD | MED HRD | MED HRD |
| Kernel Shape | MED FLT | MED FLT | LRG FLT |

TABLE 4-continued

| TRAIT | 5953 | 5962 | 95407 |
|---|---|---|---|
| Color of Kernel Cap | 5 | 3 | 3 |
| Color of Kernel Sides | 4 | 3 | 3 |

DEFINITIONS FOR TABLE 4

Emergence Vigor. Rating scale of 1=Best to 5=Slowest emergence speed and uniformity of emergence.

GDU 50% Pollen. Growing Degree Units from emergence of the plant to the stage at which 50% of the plants are shedding pollen.

GDU 50% Silk. Growing Degree Units from emergence of the plant to the stage at which 50% of the plants have exposed silks.

CALCULATION OF GROWING DEGREE UNITS FOR ONE DAY $$GDUs = \frac{\text{Temp. Max} + \text{Temp. Min}}{2} - 50$$

Enter the maximum temperature during the 24 hour period. If the maximum exceeds 86 degrees F., then enter 86. If the minimum temperature is less than 50 degrees F., then enter 50.

Plant Color. Color rating at flowering. SG=Soft Green, M=Medium Green ML=Medium Light Green, MD=Medium Dark Green, D=Dark Green Silk Color. Silk color is rated three days after the silks have fully emerged. 1=Pale Green, 2=Salmon, 3=Reddish, 4=Red, 5=Purpling, 6=Purple Leaf Orientation. Measured for the leaf above the upper ear. The measurement is in degrees from horizontal.

Leaf Width. The widest point of the leaf located at the upper ear measured in centimeters.

Number of Leaves. The physical count of the number of leaves above the upper ear node of attachment.

Tassel Type. 1=Free Standing, 5=Semi-open, 9=Shedding in the Whorl.

Tassel Size. 1=Small, 5=Medium, 9=Large

Tassel Length. Tassel length is measured from the top leaf collar to the tip of the tassel. The measurement is in centimeters.

Tassel Branch Number. This is the number of branches that originate from the main spike.

Plant Height. Measured in centimeters from the soil level to the tip of the tassel.

Ear Height. Measured in centimeters from the soil level to the upper ear node of attachment.

Stalk Diameter. Measured in millimeters in the center of the first full internode above the soil.

Shank Length. Measured in centimeters from the attachment to the stalk to the attachment to the ear.

Husk Leaves. Listed as a percent of plants demonstrating husk leaves.

Ear Attitude. Rating is taken at 65 days after 50% silk.
1=Upright, 2=Horizontal, 3=Pendent Glume Color. Color of the glumes of the tassel florets once the florets have emerged.
1=Green, 2=Light Red, 3=Red, 4=Light Purple, 5=Purple Glume Band Color. Color of the glume bands on the tassel florets.
1=Green, 2=Light Red, 3=Red, 4=Purple Anthocyanin TC. Anthrocyanin color in the top leaf collar.
Yes=Present, No=Not Present Anthocyanin Base. Anthrocyanin presence in the brace roots.
Yes=Present, No=Not Present Anthocyanin in Nodes. Anthrocyanin presence in the nodes of the stalk.
Yes=Present, No=Not Present Intactness Rating. This is a visual rating that takes place at harvest time. The scale is 1 to 9. 1=Best Ear Type. The shape of the dry ear before shelling. Cylindric or conical.

Kernel Rows. A physical count of the number of kernel rows at the midpoint of the ear.

Kernel Width. The kernels at the midpoint of the ear measured in millimeters

Kernel Length. The kernels at the midpoint of the ear measured in millimeters

Kernel Thickness. The kernels at the midpoint of the ear measured in millimeters Cob Diameter. The measurement is taken in millimeters at the midpoint of the cob.

Cob Color. Color of the dry cob when shelled.
1=White, 2=Pink, 3=Red, 4=Dark Red, 5=Other Weight of 100 Kernels. Weight in grams of a 100 kernel sample of shelled grain from an ear.

Grain Texture. This is a visual rating based on the hardness appearance of the endosperm.
S=Soft, MS=Medium Soft, Med=Medium, MED HRD=Medium Hard, H=Hard Kernel Shape. Visual shape of the majority of the kernels on an ear.
SM=Small, MED=Medium, LRG=Large, FLT=Flat, RND=Round Color of Kernel Cap. Color of the cap or crown portion of the kernel.
1=White, 2=Light yellow, 3=Bright Yellow, 4=Dark Yellow, 5=Reddish, 6=Other Color of Kernel Sides. Color of the side of the kernel at the midpoint between the tip and crown.
1=White, 2=Light yellow, 3=Bright Yellow, 4=Dark Yellow, 5=Reddish, 6=Other

DISEASE EVALUATION RATINGS

Disease evaluation ratings were conducted by Professional Seed Research, Inc., 7 South 437 Dugan Road, Sugar Grove, Ill. 60554. The evaluations are listed in Table 5.

These evaluations indicate the ratings of 5953 along with the ratings of two of the next closest genotypes. 5953 exhibited resistant reactions to five of the diseases and intermediate reactions to three of the diseases.

TABLE 5

| HY-BRID | DISEASE RATINGS | | | | | | | |
|---|---|---|---|---|---|---|---|---|
| | NLB2 | SLB0 | NLS4 | GLS | NLB1 | NLS3 | EYE | STEW |
| 5953 | 2 | 2 | 2 | 2 | 3 | 2 | 3 | 3 |
| 5962 | 3 | 2 | 3 | 3 | 3 | 2 | 4 | 2 |
| 95407 | 2 | 2 | 2 | 2 | 2 | 2 | 3 | 2 |
| P3394 | 2 | 2 | 2 | 4 | 2 | 2 | 4 | 2 |

DEFINITIONS FOR TABLE 5

RATING SCALE:
1=Highly resistant, resulting in no lesions when inoculated.
2=Resistant reaction, limiting the pathogen to only a few limited sized lesions.
3=Intermediate, will look bad visually, but no significant performance damage.
4=Susceptible reaction, performance damage will result at this level.
5=Extremely susceptible, significant yield loss and stalk damage are expected.

DISEASES:
NLB2=Northern Corn Leaf Blight, *Helminthosporium turcicum*, Race 2.
SCL0=Southern Corn Leaf Blight, *Helminthosporium maydis*, Race 0.
NLS4=Northern Leaf Spot Race 4, *Helminthosporium carbonum* (*Bipolaris zeicola*).
GLS=Grey Leaf Spot, *Cercospora zeae-maydis*.
NLB1=Northern Leaf Blight, *Helminthosporium turcicum*, (*Exserohilum turcicum*), Race 1.
NLS3=Northern Leaf Spot Race 3, *Helminthosporium carbonum* (*Bipolaris zeicola*).
EYE=Eyespot, *Kabatiella zeae*.
STEW=Stewarts Bacterial Wilt, *Erwinia stewartii*.

The three varieties studied in tables 4 and 5 are closely related. All three have the same maternal parent. Pioneer 3394 is the largest sales volume competitive hybrid for the north central United States. Hybrid 5962 is a commercially available line sold by Great Lakes Hybrid. Hybrid 95407 is a proprietary hybrid which is a cross of the maternal parent of 5953 with a sibling of the paternal parent of hybrid 5953. While hybrid 95407 has good resistance to grey leaf spot, it did not have the other characteristics that are demanded by the farmers of the north central United States. In particular, hybrid 5953, when compared to 95407, has superior yield, matures 3 days earlier, has stronger roots and a better stalk. In contrast to hybrid 5962, hybrid 5953 has superior disease resistance, yields are slightly improved, stalk lodging is reduced and plant intactness has been improved.

Based upon the above study, hybrid 5953 is a significantly superior variety as compared to our closest related hybrids both publicly available and proprietary hybrids. In contrast to commercially available, Pioneer variety #3394, hybrid 5953 has a superior resistance to grey leaf blight, as noted in Table 5. Hybrid 5953 has superior yield to #3394 as noted in Table 6. This yield difference is more pronounced when grey leaf blight is present. Hybrid 5953 has a maturing date that falls between the two Pioneer varieties—with #3394 being slightly earlier and #3335 being later maturing. Pioneer hybrid 3335 is significantly weaker in stalk quality as indicated by the % SL (percent stalk lodging counts).

TABLE 6

| HYBRID | LOC | No. 2 YIELD | MOIS | POPUL | % RL | % SL | TW |
|---|---|---|---|---|---|---|---|
| 5953 | 49 | 168.5 | 21.91 | 26,132 | 2.6 | 1.2 | 54.5 |
| P3394 | 49 | 160.8 | 21.35 | 25,725 | 6.6 | 3.8 | 54.7 |
| P3335 | 49 | 170.4 | 22.91 | 26,161 | 2.8 | 5.4 | 54.2 |

INDUSTRIAL APPLICABILITY

Corn is used as human food, livestock feed, and as raw material in industry. The food uses of corn, in addition to human consumption of corn kernels, include both products of dry-milling and wet-milling industries. The principal products of corn dry-milling are grits, meal, and flour. The corn wet-milling industry can provide corn starch, corn syrups, and dextrose for food use. Corn oil is recovered from corn germ, which is a by-product of both dry-milling and wet-milling industries.

Corn, including both grain and non-grain portions of the plant, is also used extensively as livestock feed, primarily for beef cattle, dairy cattle, hogs, and poultry. Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include de-icing products, plant fertilizer products and herbicide products.

Plant parts other than the grain of corn are also used in the industry. Stalks and husks are made into paper and wallboard and cobs are used for fuel to make charcoal. Cobs are also used as a carrier in other non-grain commercial products. The grain and the plant parts that are produced from the cultivation of 5953 can be utilized for human food, livestock feed, and as a raw material in the industry.

Hybrid 5953 can also be used to develop novel corn varieties. Standard breeding techniques can be used to isolate select qualities from hybrid 5953 for placement into new lines of inbred corn. Typical of these techniques is the recurrent and donor type breeding process. In addition, the hybrid 5953 can be used as starting material to generate embryonic callus and cell suspensions. These cells can be used for a variety of known genetic techniques. Examples of the power of this new technology can be found in U.S. Pat. Nos. 5,134,074 entitled "Embryogenic callus and cell suspensions of corn inbred B73" and 5,484,956 entitled "Fertile transgenic *zea mays* plant comprising heterologous DNA encoding *Bacillus thuringiensis* endotoxin."

DEPOSITS

Applicants have made available to the public without restriction a deposit of at least 2500 F1 seeds of Hybrid 5953 with the American Type. Culture Collection (ATCC), 10801 University Blvd., Manassas, Va. 20110-2209. The deposit was made on Jul. 28, 1998, and assigned Accession No. 203075.

The seed deposited with the ATCC are taken from the same deposit maintained by Great Lakes Hybrids, Inc. at 972 County Road, 500 East, Ivesdale, Ill. 61851. This deposit of the Hybrid 5953 will be maintained without restriction in the ATCC depository for a period of 30 years, or five years past the most recent request, or for the effective life of the patent, whichever is longer, and will be replaced if the ATCC depository seed becomes nonviable during that time.

What is claimed is:

1. Hybrid corn seed designated as 5953 and having ATCC Accession No 203075.

2. A corn plant produced by the seed of claim 1.

3. A corn plant having the physiological and morphological characteristics of the plant of claim 2.

4. A tissue culture of regenerable cells of a plant according to claim 2 wherein the tissue regenerates plants having all morphological and physiological characteristics of hybrid 5953.

5. A corn plant regenerated from the tissue culture of claim 4 said plant possessing all morphological and physiological characteristics of hybrid 5953.

6. A method of producing corn seeds comprising the steps of sexually crossing two corn varieties wherein at least one of the two varieties is hybrid 5953 and having ATCC Accession No. 203075, and harvesting the seed produced from the crossing step.

7. Hybrid seed produced by crossing the plant of claim 2 with a corn plant, said hybrid seed having 50% of its genome contributed by the plant of claim 2.

* * * * *